(12) United States Patent
Hara et al.

(10) Patent No.: US 6,528,601 B1
(45) Date of Patent: Mar. 4, 2003

(54) POLYMERIZABLE SULFUR-CONTAINING (METH) ACRYLATE, POLYMERIZABLE COMPOSITION AND OPTICAL LENS

(75) Inventors: Tadashi Hara, Tokuyama (JP); Katsuhiro Mori, Tokuyama (JP)

(73) Assignee: Tokuyama Corporation, Yamaguchi (JP)

( * ) Notice: Subject to any disclaimer, the term of this patent is extended or adjusted under 35 U.S.C. 154(b) by 342 days.

(21) Appl. No.: 09/645,363

(22) Filed: Aug. 25, 2000

(30) Foreign Application Priority Data

Aug. 26, 1999 (JP) ............................... 11-240035

(51) Int. Cl.[7] ................ C08F 28/06; C07D 339/08; G02B 1/04
(52) U.S. Cl. ............... 526/256; 351/159; 549/16; 549/17; 549/15
(58) Field of Search .................. 526/256; 549/16, 549/17, 15; 351/159

(56) References Cited

U.S. PATENT DOCUMENTS 4,939,218 A 7/1990 Kawaki et al.

FOREIGN PATENT DOCUMENTS

| DE | 3838350 A1 | 5/1989 |
|----|------------|--------|
| JP | 1128966 | 5/1989 |
| JP | 4161410 | 6/1992 |
| JP | 4161411 | 6/1992 |
| JP | 812669 | 1/1996 |

OTHER PUBLICATIONS

Patent Abstracts of Japan; vol. 014, No. 236, May 18, 1990.

Patent Abstracts of Japan; vol. 016, No. 461, Sep. 25, 1992.

Patent Abstracts of Japan; vol. 1996, No. 05, May 31, 1996.

*Primary Examiner*—Christopher Henderson
(74) *Attorney, Agent, or Firm*—Birch, Stewart, Kolasch & Birch, LLP

(57) ABSTRACT

There is disclosed a polymerizable sulfur-containing (meth) acrylate, it has a high refractive index, a great Abbe's number and excellent light resistance and is suitable for the production of a transparent resin which rarely smells at the time of molding and is further excellent in storage stability. A polymerizable composition containing the (meth)acrylate and an optical lens which is a cured product of the composition are also disclosed.

11 Claims, 2 Drawing Sheets

POLYMERIZABLE SULFUR-CONTAINING (METH) ACRYLATE, POLYMERIZABLE COMPOSITION AND OPTICAL LENS

DETAILED DESCRIPTION OF THE INVENTION

The present invention relates to a polymerizable sulfur-containing (meth)acrylate, a polymerizable composition comprising the same and an optical lens which is a cured product of the composition. More specifically, it relates to a polymerizable sulfur-containing (meth)acrylate which has a high refractive index, a great Abbe's number and excellent light resistance, is suitable for the production of a transparent resin which rarely smells at the time of molding and is further excellent in storage stability, a polymerizable composition comprising the (meth)acrylate and an optical lens which is a cured product of the composition.

Although various kinds of organic glass have been studied as substitutes for inorganic glass, they still have many defects and completely satisfactory organic glass is yet to be obtained. For example, cured materials obtained by polymerizing monomers essentially composed of methyl methacrylate and diethylene glycol bis(allylcarbonate) are used as optical materials and lenses but their refractive indices are low at approximately 1.50.

Various studies on the introduction of a sulfur atom into the molecular structure have recently been made to improve refractive index. JP-A 1-128966 (the term "JP-A" as used herein means an "unexamined published Japanese patent application") discloses a (meth)acrylate-based polymerizable monomer having a sulfide structure. JP-A 4-161410 discloses a polymer obtained by polymerizing and curing a (meth)acrylate-based polymerizable monomer having a dithian ring. Cured materials obtained by polymerizing and curing these polymerizable monomers have a refractive index of approximately 1.57 to 1.61 which are a little higher than the conventional cured products. Therefore, it is hardly said that they are satisfactory in terms of refractive index.

Further, JP-A 4-161411 discloses a polymer obtained by polymerizing and curing a thio(meth)acrylate-based polymerizable monomer having a dithian ring. Although this cured product has a high refractive index of 1.60 to 1.65, it has poor light resistance and emits an offensive smell at the time of molding. The thio(meth)acrylate-based polymerizable monomer also has such a problem that it is readily gelled when it is stored.

JP-A 8-12669 discloses an aromatic vinyl compound having a dithian ring. A cured product obtained by polymerizing and curing this compound has a high refractive index of 1.66 but its Abbe's number is 31. Therefore, the improvement of its Abbe's number is desired.

It is an object of the present invention to provide a polymerizable monomer which solves the above problems of the conventional polymerizable monomer for use as an optical material and which provides a cured product having a high refractive index, a great Abbe's number and excellent light resistance, rarely smells at the time of molding and is further excellent in storage stability.

It is another object of the present invention to provide a specific (meth)acrylate having a dithian ring as a polymerizable monomer having the above characteristic properties.

It is still another object of the present invention to provide a polymerizable composition comprising the above polymerizable monomer.

It is a further object of the present invention to provide a cured material for use as an optical material which is a cured product of the above polymerizable composition.

It is a still further object of the present invention to provide an optical lens which comprises the above cured material.

Other objects and advantages of the present invention will become apparent from the following description.

According to the present invention, firstly, the above objects and advantages of the present invention are attained by a polymerizable sulfur-containing (meth)acrylate represented by the following formula (1):

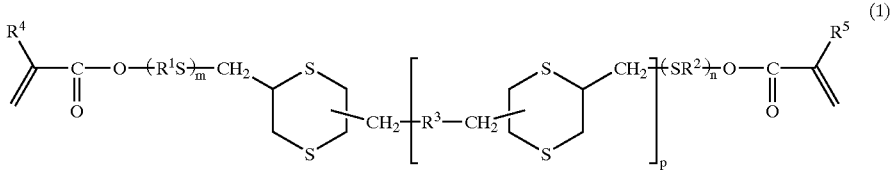

wherein $R^1$ and $R^2$ are each independently an alkylene group having 2 to 4 carbon atoms or arylene group having 6 to 12 carbon atoms, $R^3$ is a group represented by the following formula (a):

wherein $R^6$ is an alkylene group having 2 to 4 carbon atoms, arylene group having 6 to 12 carbon atoms, aromatic heterocyclic group, or group represented by the following formula (b):

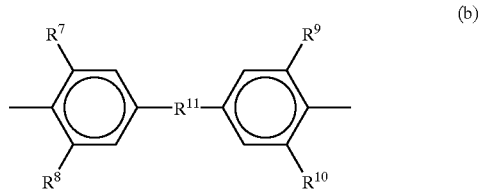

wherein $R^7$, $R^8$, $R^9$ and $R^{10}$ are each independently a halogen atom (excluding fluorine atom) or hydrogen atom, $R^{11}$ is an alkylene group having 1 to 3 carbon atoms or sulfur atom, and q is an integer of 0 to 4), $R^4$ and $R^5$ are each independently a hydrogen atom or methyl group, p is an integer of 0 to 6, and m and n are each independently an integer of 1 to 6, with the proviso that the above alkylene group, arylene group and aromatic heterocyclic group may be substituted with a substituent, and m and n are not "1" when p is "0".

Secondly, the above objects and advantages of the present invention are attained by a polymerizable composition which comprises a polymerizable sulfur-containing (meth) acrylate represented by the above formula (1) in an amount of 10 to 98 wt % and other polymerizable monomer copolymerizable with the above (meth)methacrylate in an amount of 90 to 2 wt % based on the total weight of the (meth)acrylate and the monomer.

Thirdly, the above objects and advantages of the present invention are attained by a cured material for use as an optical material which is a cured product of the polymerizable composition of the present invention.

In the fourth place, the above objects and advantages of the present invention are attained by an optical lens which is the cured material for use as an optical material of the present invention.

Figure 1:
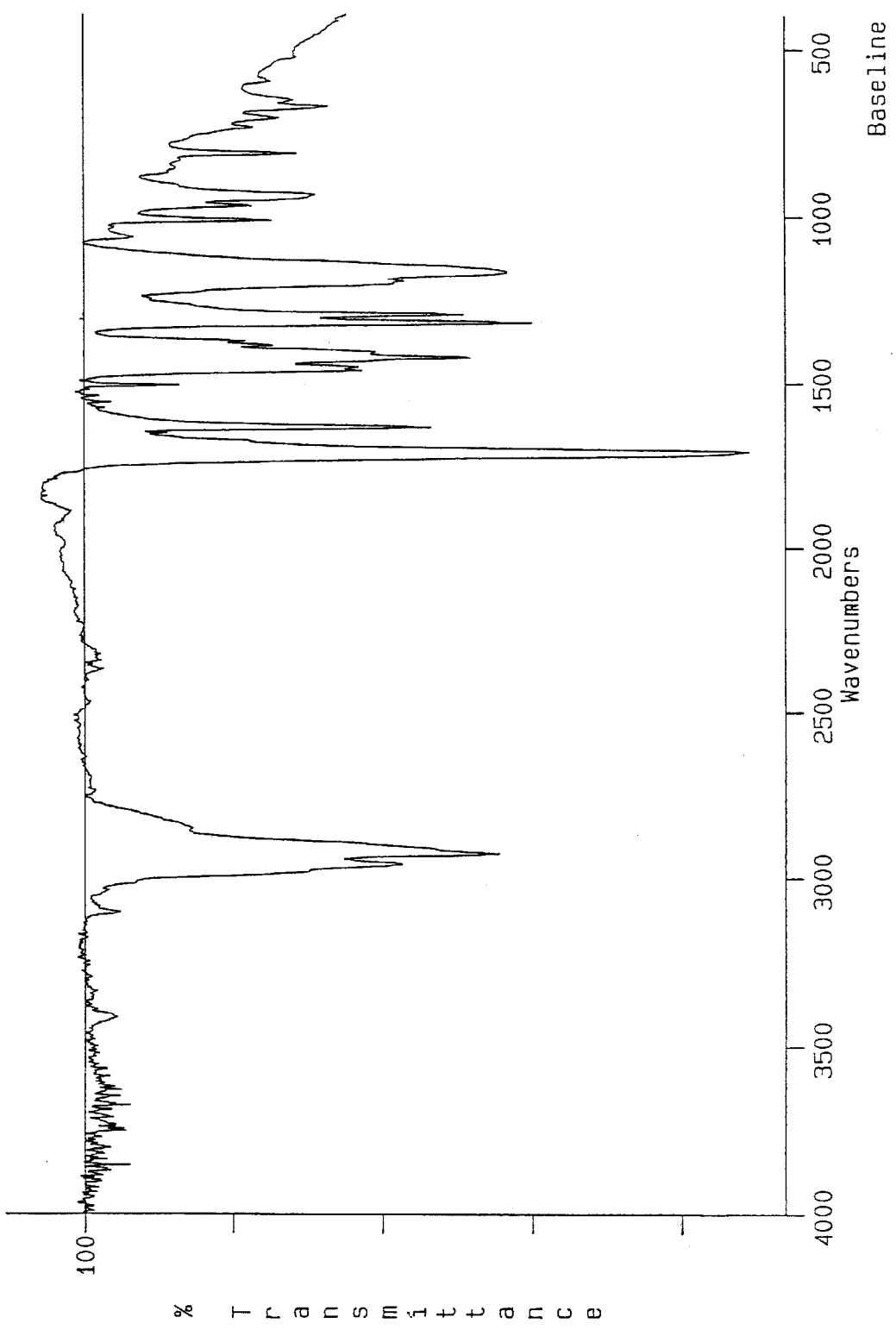
FIG. 1 shows the infrared absorption spectrum of a compound (η) which is the product of Example 1.

The present invention will be described hereinafter.

The polymerizable sulfur-containing (meth)acrylate of the present invention is represented by the above formula (1).

In the above formula (1), $R^1$ and $R^2$ are each independently an alkylene group having 2 to 4 carbon atoms or arylene group having 6 to 12 carbon atoms. They may be substituted by a substituent.

Examples of the alkylene group having 2 to 4 carbon atoms include ethylene group, propylene group, isopropylene group, butylene group and the like. Out of these, ethylene group is preferred because a cured material having a high refractive index is obtained. Examples of the arylene group having 6 to 12 carbon atoms include phenylene group, tolylene group, xylylene group, naphthylene group and the like. Known groups may be used as the substituents which can substitute the alkylene group and arylene group without restriction, out of which alkyl groups, aryl groups, aralkyl groups, alkoxy groups, alkylthio groups, aromatic heterocyclic groups and halogen atoms excluding fluorine are preferred. These substituents will be described hereinafter.

Known alkyl groups may be used as the substituents without restriction, out of which alkyl groups having 1 to 4 carbon atoms such as methyl group, ethyl group, propyl group, isopropyl group, butyl group and t-butyl group are preferred.

Known aryl groups may be used as the substituents without restriction, out of which aryl groups having 6 to 12 carbon atoms such as phenyl group, tolyl group and naphthyl group are preferred.

Known aralkyl groups may be used as the substituents without restriction, out of which aralkyl groups having 7 to 11 carbon atoms such as benzyl group and phenethyl group are preferred.

Known alkoxy groups may be used as the substituents without restriction, out of which alkoxy groups having 1 to 4 carbon atoms such as methoxy group, ethoxy group, propoxy group, isopropoxy group, butoxy group and t-butoxy group are preferred.

Known alkylthio groups may be used as the substituents without restriction, out of which alkylthio groups having 1 to 4 carbon atoms such as methylthio group, ethylthio group, propylthio group, isopropylthio group, butylthio group and t-butylthio group are preferred.

Known aromatic heterocyclic groups may be used as the substituents without restriction, out of which aromatic heterocyclic groups having 4 to 10 carbon atoms such as thienyl group, furyl group and benzothienyl group are preferred.

The halogen atoms excluding fluorine as the substituents are chlorine, bromine and iodine, out of which bromine is preferred from the viewpoints of the refractive index and light resistance of the obtained cured product and bromine substituted for an arylene group is more preferred.

The number of the substituents is at least 1, preferably 4 or less from the viewpoint of refractive index. When the number of the substituents is 2 or more, they may differ from one another.

When $R^1$ and $R^2$ are a substituted arylene group, an arylene group substituted by bromine is preferable.

$R^3$ in the above formula (1) is a group represented by the following formula (a).

(a)

In the above formula, q representing the number of units ($-R^6-S-$) is an integer of 0 to 4. q is preferably an integer of 0 to 2 to from the viewpoint of the heat resistance of the obtained cured product. When q is "0", $R^3$ is a mere bond.

$R^6$ in the above unit is an alkylene group having 2 to 4 carbon atoms, arylene group having 6 to 12 carbon atoms, aromatic heterocyclic group or group represented by the following formula (b).

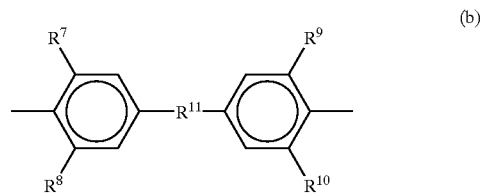

(b)

$R^7$, $R^8$, $R^9$ and $R^{10}$ in the above formula are each independently a halogen atom excluding a fluorine atom or hydrogen atom. All of them are preferably a bromine atom from the viewpoint of refractive index and light resistance. $R^{11}$ in the above formula is an alkylene group having 1 to 3 carbon atoms or sulfur atom. Examples of the alkylene group include methylene group, ethylene group and propylene group. $R^{11}$ is preferably a sulfur atom because a cured product having a high refractive index is obtained and its raw material is easily acquired or an alkylene group from the viewpoint of light resistance.

Examples of the substituents for the alkylene group and arylene group as $R^6$ are the same as those listed for $R^1$ and $R^2$. Out of these, ethylene group, isopropylene group and phenylene group are preferred from the viewpoints of balance between refractive index and Abbe's number, and ethylene group and isopropylene group are particularly preferred.

Known aromatic heterocyclic groups may be used as $R^6$ without restriction, out of which aromatic heterocyclic groups having 4 to 10 carbon atoms such as thienyl group, furyl group and benzothienyl group and these groups having one or more of the same substituents as those for $R^1$ and $R^2$ are preferred.

$R^4$ and $R^5$ in the above general formula (1) are each independently a hydrogen atom or methyl group, out of which methyl group is preferred from the viewpoint of the storage stability of the polymerizable monomer.

p representing the number of repetitions of the structural unit including a dithian ring in the above formula (1) is an integer of 0 to 6. p is preferably an integer of 0 to 3 from the viewpoint of the heat resistance of the obtained cured product. The bonding position of the groups —$CH_2$—(when p is "0") and —$CH_2$—$R^3$—$CH_2$—(when p is an integer other than "0") bonded to the dithian ring in the above formula (1) may be a position where each dithian ring becomes 2,5-substituted 1,4-dithian ring or 2,6-substituted 1,4-dithian ring. When p is an integer of 2 or more, the bonding position may be a position where these rings are mixed arbitrarily.

m and n which represent the numbers of repetitions of the unit (—$R^1$—S—) and the unit (—$R^2$—S—) in the above formula (1), respectively, differ according to the value of p. That is, when p is "0", m and n are each independently an integer of 2 to 6 and when p is not "0", m and n are each independently an integer of 1 to 6. From the viewpoint of the heat resistance of the obtained cured product, m and n are preferably an integer of 2 to 4 when p is "0" and an integer of 1 to 4 when p is not "0".

Out of the polymerizable sulfur-containing (meth) acrylates of the present invention represented by the above formula (1), polymerizable sulfur-containing (meth) acrylates represented by the following formula (2) are more preferred because their raw materials are easily acquired and synthesized.

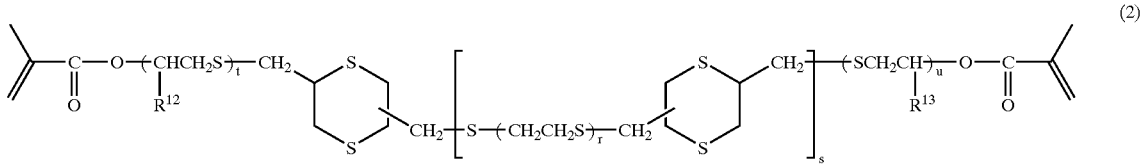

(2)

In the above formula, $R^{12}$ and $R^{13}$ are each independently a hydrogen atom or methyl group, r is an integer of 0 to 2, s is an integer of 0 to 3, and t and u are each independently an integer of 1 to 4, with the proviso that when s is "0", t and u cannot be 1.

Stated more specifically, the polymerizable sulfur-containing (meth)acrylates of the present invention have the following structures.

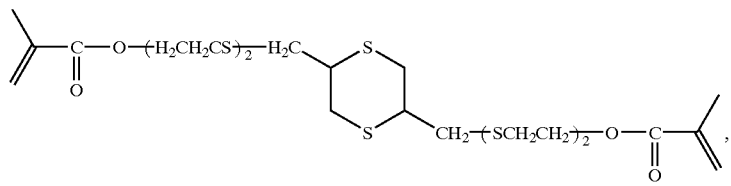

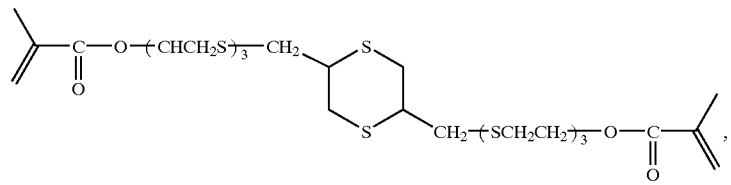

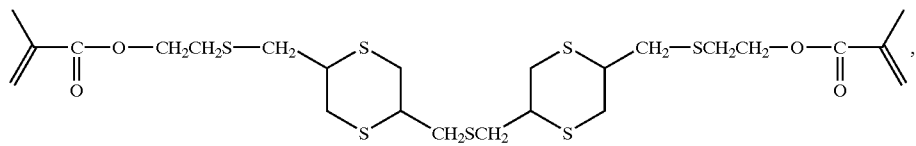

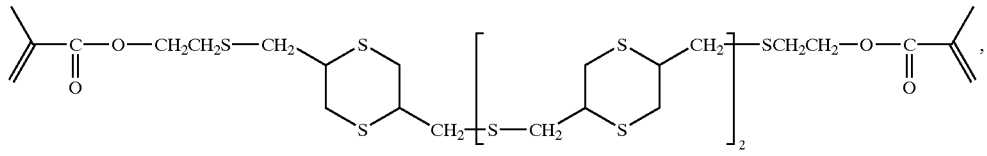

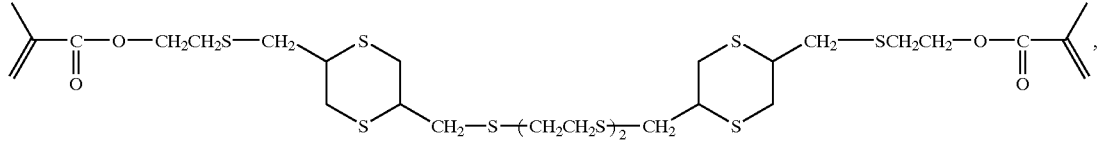

-continued

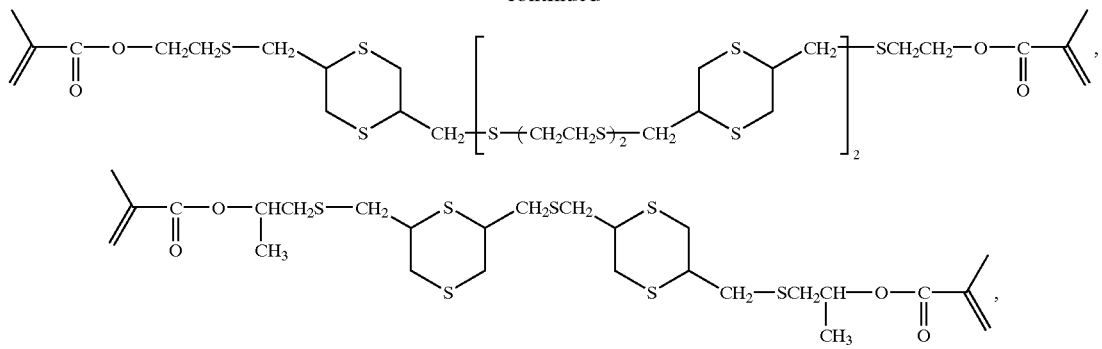

The structures of the polymerizable sulfur-containing (meth)acrylates of the present invention can be identified and confirmed by the following means, for example.

(A) When the infrared absorption spectrum (IR) of each of the polymerizable sulfur-containing (meth)acrylates is measured, an absorption based on a terminal unsaturated hydrocarbon group can be observed at 1,600 to 1,650 cm$^{-1}$ and a strong absorption based on the carbonyl group of an ester bond can be observed at around 1,700 to 1,750 cm$^{-1}$.

(B) The bonding manner of a hydrogen atom existent in the monomer can be known by measuring the $^1$H-nuclear magnetic resonance spectrum ($^1$H-NMR) of the polymerizable sulfur-containing (meth)acrylate.

(C) The percentage by weight of oxygen can be calculated by obtaining percentages by weight of carbon, hydrogen, sulfur and other elements (nitrogen, halogen) by elemental analysis and subtracting the total of these from 100 so as to determine the compositional formula of the monomer.

The process for producing the polymerizable sulfur-containing (meth)acrylate of the present invention is not particularly limited but the polymerizable sulfur-containing (meth)acrylate of the present invention can be generally produced by the following two processes (A) and (B).

Production Process (A)

This production process is to produce a polymerizable sulfur-containing (meth)acrylate represented by the above formula (1) by reacting a bifunctional mercapto compound having a dithian ring represented by the following formula (3):

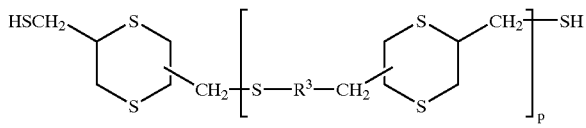

(3)

wherein R$^3$ and p are as defined in the above formula (1), a halogenoalcohol represented by the following formula (4):

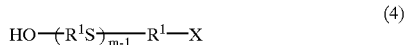

(4)

wherein R$^1$ and m are as defined in the above formula (1), and X is a halogen atom excluding fluorine, and a halogenoalcohol represented by the following formula (5):

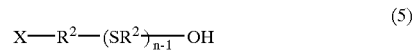

(5)

wherein R$^2$ and n are as defined in the above formula (1), and X is a halogen atom excluding fluorine, in the presence of a basic compound (dehydrohalogenation/substitution reaction) to obtain a bifunctional hydroxy compound (may be simply referred to as "diol" hereinafter) and subjecting the bifunctional hydroxy compound to an ester exchange reaction with a (meth)acrylic ester.

The bifunctional mercapto compound having a dithian ring represented by the above formula (3) can be obtained by the following method. For example, 2,5-bis (mercaptomethyl)-1,4-dithian is obtained by reacting 3-chloro-1-propene with sodium disulfide to synthesize allyl disulfide and then reacting allyl disulfide with sulfuryl chloride. This 2,5-bis(chloromethyl)-1,4-dithian is then reacted with thiourea and the reaction product is hydrolyzed to obtain 2,5-bis(mercaptomethyl)-1,4-dithian.

The halogenoalcohols represented by the above formulas (4) and (5) can be obtained by the following method. For example, the following compound can be obtained by reacting 1,2-ethanedithiol with 1-chloroethanol and then with 1,2-dichloroethane.

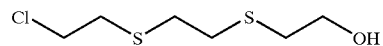

Production Process (B)

This production process is to produce a polymerizable sulfur-containing (meth)acrylate represented by the above formula (1) by reacting a bifunctional halide having a dithian ring represented by the following formula (6):

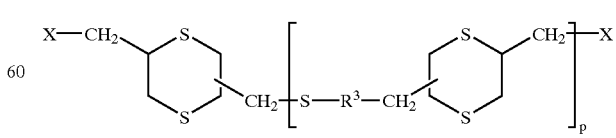

(6)

wherein R$^3$ and p are as defined in the above formula (1), and X is a halogen atom excluding fluorine, a mercaptoalcohol represented by the following formula (7):

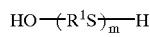

wherein $R^1$ and m are as defined in the above formula (1), and a mercaptoalcohol represented by the following formula (8):

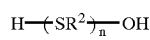

wherein $R^2$ and n are as defined in the above formula (1), in the presence of a basic compound (dehydrohalogenation/substitution reaction) to obtain a diol, and carrying out an ester exchange reaction between the diol and a (meth)acrylic ester.

The bifunctional halide having a dithian ring represented by the above formula (6) can be obtained by the following method. For example, 2,5-bis(chloromethyl)-1,4-dithian can be obtained by reacting 3-chloro-1-propene with sodium disulfide to synthesize allyl disulfide and then reacting allyl disulfide with sulfuryl chloride.

The mercaptoalcohols represented by the above formulas (7) and (8) can be obtained by the following method. For example, the following compound can be obtained by reacting dimercaptodiethylene sulfide with 2-chloroethanol.

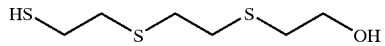

The above production processes (A) and (B) are aimed to produce a polymerizable sulfur-containing (meth)acrylate represented by the above formula (1) of interest by obtaining a diol through the dehydrohalogenation/substitution reaction of the first stage and esterifying the diol through an ester exchange reaction using a (meth)acrylic ester as the reaction of the second stage. The reaction conditions of these reactions are not particularly limited but general reaction conditions are as follows.

That is, in the dehydrohalogenation/substitution reaction of the first stage, hydrogen halide is formed along with the proceeding of the reaction. Therefore, it is generally carried out in the presence of a basic compound for capturing it. Examples of the basic compound include alkali metal hydroxides such as lithium hydroxide, sodium hydroxide and potassium hydroxide; alkali metal salts of alcohols such as lithium methoxide, sodium methoxide, sodium ethoxide and t-butoxy potassium; and organic bases such as triethylamine, pyridine and quinoline.

A solvent is preferably used in the above reaction to dissolve the basic compound when the basic compound is solid. Preferred examples of the solvent include water, methanol, ethanol, isopropanol and the like. A solvent is preferably used when the compounds represented by the above formulas (3) to (8) are solid. Preferred examples of the solvent include alcohols such as methanol, ethanol and isopropanol; ethers such as diethyl ether, tetrahydrofuran and dioxane; halides such as methylene chloride and chloroform; and aliphatic and aromatic hydrocarbons such as hexane, heptane, benzene and toluene.

The reaction temperature differs according to the types of raw materials and the types of solvents but it is preferably 20 to 100° C. The reaction time also differs according to the types of raw materials but it is generally 10 minutes to 48 hours, preferably 1 to 24 hours. During the reaction, stirring is preferably carried out.

The molar ratio of the compounds in the reaction may be suitably determined as required. In the case of the production process (A), the total of the numbers of mols of the compounds represented by the above formulas (4) and (5) becomes preferably 2 times the number of mols of the compound represented by the above formula (3). In the case of the production process (B), the total of the number of mols of the compounds represented by the above formulas (7) and (8) becomes preferably 2 times the number of mols of the compound represented by the above formula (6).

Known (meth)acrylic esters may be used in the ester exchange reaction of the second stage without restriction. However, since an unreacted (meth)acrylic ester is removed after the end of the reaction, a low-boiling compound is preferably used. Similarly, an alcohol (by-product) derived from the (meth)acrylic ester as a raw material must be removed. Therefore, a (meth)acrylic ester having an alcohol residual group which by-produces an alcohol having a low molecular weight and low boiling point is more preferably used. From the above point of view, the (meth)acrylic ester is preferably a monofunctional (meth)acrylic ester such as methyl (meth)acrylate, ethyl (meth)acrylate, propyl (meth)acrylate or butyl (meth)acrylate. Out of these, methyl (meth)acrylate is the most preferred as an industrial raw material because it has a low boiling point, is easily removed from a reaction system and is inexpensive.

The above ester exchange reaction is generally carried out using a catalyst. Examples of the catalyst include acidic catalysts such as sulfuric acid and p-toluenesulfonic acid; and basic catalysts such as potassium alkoxide, sodium alkoxide, cesium hydroxide, potassium hydroxide, sodium hydroxide, lithium hydroxide, cesium carbonate and potassium carbonate. Considering the reaction rate, basic catalysts are preferred, out of which basic cesium compounds such as cesium hydroxide and cesium carbonate are particularly preferred.

The above ester exchange method can be carried out using various solvents. Preferred examples of the solvent include hydrocarbon-based solvents such as pentane, hexane, cyclohexane, heptane, benzene, toluene and xylene; ether-based solvents such as ethyl ether, tetrahydrofuran and dioxane; and halogen-based solvents such as dichloromethane, chloroform, tetrachloroethylene, chlorobenzene and o-dichlorobenzene. These solvents may be selected according to the catalyst used but hydrocarbon-based solvents are preferred and aliphatic hydrocarbon-based solvents such as hexane and heptane are more preferred.

The ester exchange reaction temperature is not particularly limited but it is preferably 0 to 200° C., more preferably 30 to 150° C. The reaction time, which differs according to the reaction temperature and required reaction yield, is preferably 1 to 50 hours.

To prevent the gelation of the reaction product, a polymerization inhibitor is desirably added in the above ester exchange method. Known polymerization inhibitor compounds may be used without restriction. Examples of the polymerization inhibitor include phenolic polymerization inhibitors such as hydroquinone, p-methoxyphenol, 2,6-di-t-butyl-4-methylphenol and p-t-butylcatechol; phenothiazine, copper chloride (II), iron chloride (III) and the like. Out of these, p-methoxyphenol and p-t-butylcatechol are preferred in consideration of polymerization inhibition capacity, the color development of the product and the removal of the inhibitor from the reaction product after the reaction. The amount of the polymerization inhibitor which differs according to its type and the reaction temperature is preferably 0.01 to 10 wt %, more preferably 0.1 to 5 wt % based on the diol as a raw material.

Since the above ester exchange reaction is an equilibrium reaction, the reaction is preferably carried out while an alcohol by-produced by the reaction is removed from a reaction system in order to carry out the reaction quickly at a high yield. Known methods for removing the alcohol may be used without restriction. The methods include distillation, adsorption using an adsorber such as a molecular sieve, and the like. When the alcohol is removed by distillation, an apparatus equipped with a fractionating column is preferably used to separate it from the solvent used in the reaction.

The polymerizable sulfur-containing (meth)acrylate of the present invention represented by the above formula (1) produced by any one of the above production processes is isolated as required and used. Known isolation methods may be used without restriction. For example, when purification operation and decoloration operation are not particularly required because of a high reaction yield, an unreacted (meth)acrylic ester compound and the solvent may be simply distilled off after the catalyst is removed by filtration. When the reaction yield is low or color development causes a problem, known purification operation such as distillation or column chromatography, a treatment with an adsorber such as activated carbon or silica, or known decoloration operation such as washing with water, hydrochloric acid water or sodium hydroxide aqueous solution may be suitably selected and carried out.

The polymerizable sulfur-containing (meth)acrylate of the present invention provides a cured product which has a high refractive index, a large Abbe's number and excellent light resistance and rarely smells at the time of molding through polymerization and curing.

The polymerizable sulfur-containing (meth)acrylate of the present invention can be advantageously used as an optical material, particularly a raw material for lenses, making use of the above characteristic properties obtained when it is homopolymerized. When the polymerizable sulfur-containing (meth)acrylate of the present invention is used for such application purposes, the polymerizable sulfur-containing (meth)acrylate of the present invention and other unsaturated monomer (also called "comonomer" hereinafter) copolymerizable therewith are preferably used and copolymerized in consideration of other physical properties such as refractive index, Abbe's number and light resistance.

The comonomer is not particularly limited if it is a polymerizable monomer copolymerizable with the polymerizable sulfur-containing (meth)acrylate of the present invention. An appropriate comonomer which gives required physical properties according to the targeted application purpose may be suitably selected and used. Illustrative examples of the comonomer suitable when the (meth)acrylate of the present invention is used as an optical material include (meth)acrylic esters such as methyl (meth)acrylate, benzyl (meth)acrylate, phenyl (meth)acrylate, 2-hydroxyethyl (meth)acrylate, ethylene glycol di(meth)acrylate, diethylene glycol di(meth)acrylate, triethylene glycol di(meth)acrylate, tetraethylene glycol di(meth)acrylate, glycidyl (meth)acrylate, bisphenol A di(meth)acrylate, 2,2-bis(4-(meth)acryloyloxyethoxyphenyl)propane and 2,2-bis(3,5-dibromo-4-(meth)acryloyloxyethoxyphenyl)propane; thio(meth)acrylic esters such as methyl thio(meth)acrylate, phenyl thio(meth)acrylate, benzyl thio(meth)acrylate, ethane dithiol dithio(meth)acrylate, benzene dithiol dithio(meth)acrylate and xylylene dithiol dithio(meth)acrylate; allyl compounds such as diallyl phthalate, diallyl terephthalate, dially isophthalate, diallyl tartrate, diallyl epoxysuccinate, diallyl malate, allyl cinnamate, allyl isocyanurate, diallyl chlorendate, diallyl hexaphthalate, diallyl carbonate and allyl diglycol carbonate; aromatic vinyl compounds such as styrene, divinyl benzene, chlorostyrene, bromostyrene, dibromostyrene, vinyl naphthalene, isopropenyl naphthalene, α-methylstyrene and α-methylstyrene dimer; and urethane (meth)acrylates and epoxy (meth)acrylates having two or more (meth)acrylate groups in the molecule. These monomers may be used alone or in admixture of two or more.

The copolymerization ratio may be suitably determined according to application purpose. Based on the total weight of all the polymerizable monomers, the polymerizable sulfur-containing (meth)acrylate of the present invention may be used in an amount of preferably 10 to 98 wt %, particularly preferably 20 to 95 wt % (the balance consists of a comonomer).

The polymerization method for obtaining a cured product by polymerizing and curing the polymerizable sulfur-containing (meth)acrylate of the present invention or a mixture of the (meth)acrylate and a comonomer is not particularly limited and known polymerization methods may be used. Stabilizers and additives such as a release agent, ultraviolet light absorber, infrared light absorber, ultraviolet stabilizer, antioxidant, color protection agent, antistatic agent, fluorescent dye, dye, pigment, perfume, photochromic compound may be mixed as required during polymerization.

Polymerization initiating means may be use of a radical polymerization initiator such as a peroxide or azo compound, or exposure to ultraviolet radiation, α-rays, β-rays or γ-rays, or both of them.

The polymerization method is not particularly limited. When application as an optical material such as a lens is taken into consideration, cast polymerization is preferred. A typical cast polymerization method will be further detailed hereinafter.

In this method, the curable composition of the present invention containing a radical polymerization initiator is injected into a gap between molds held by an elastomer gasket or spacer, polymerized and cured by heating in an air furnace and taken out.

Known radical polymerization initiators may be used without restriction. Typical examples of the radical polymerization initiator include diacyl peroxides such as benzoyl peroxide, p-chlorobenzoyl peroxide, decanoyl peroxide, lauroyl peroxide and acetyl peroxide; peroxy esters such as t-butyl peroxy-2-ethyl hexanoate, t-butyl peroxydicarbonate, cumyl peroxyneodecanoate and t-butyl peroxybenzoate; percarbonates such as diisopropyl peroxydicarbonate, di-2-ethylhexyl peroxydicarbonate and di-sec-butyloxycarbonate; and azo compounds such as 2,2'-azobisisobutyronitrile, 2,2'-azobis(4-dimethylvaleronitrile), 2,2'-azobis(2-methylbutyronitrile) and 1,1'-azobis(cyclohexane-1-carbonitrile).

The amount of the radical polymerization initiator differs according to polymerization conditions, the type of initiator and the type and composition of the curable composition of the present invention and cannot be limited sweepingly. However, it is preferably 0.01 to 10 parts by weight based on 100 parts by weight of the total of all the polymerizable monomers.

Out of the polymerization conditions, temperature has an influence on the properties of the obtained resin. The temperature condition cannot be limited sweepingly because it is influenced by the type and amount of initiator and the types of monomers. So-called tapered two-stage polymerization is advantageously carried out to start polymerization at a relatively low temperature, elevate temperature gradually and cure the resin at a high temperature at the end of polymerization.

Since the polymerization time differs according to various factors like temperature, the optimum time is suitably predetermined according to these conditions. The polymerization conditions are preferably selected to complete polymerization in 2 to 40 hours.

Cast polymerization can be carried out by known photopolymerization using ultraviolet radiation. Benzoin, benzoin methyl ether, benzoin butyl ether, benzophenol, acetophenone, 4,4'-dichlorobenzophenone, diethoxyacetophenone, 2-hydroxy-2-methyl-1-phenylpropan-1-one, benzyl methyl ketal, 1-(4-isopropylphenyl)-2-hydroxy-2-methylpropan-1-one, 1-hydroxycyclohexylphenyl ketone, 2-isopropylthiooxanthone and the like may be used as a photopolymerization initiator. The photopolymerization initiator is preferably used in an amount of 0.001 to 5 parts by weight based on 100 parts by weight of the total of all the monomers.

The cured product of the present invention obtained by the above method can be subjected to the following treatments according to its application purpose. That is, it can be dyed with a dye such as a disperse dye, hard coated with a silane coupling agent, hard coating agent essentially composed of a sol of silicon, zirconium, antimony or aluminum oxide, or hard coating agent essentially composed of an organic polymer, anti-reflection treatment by forming a thin film of a metal oxide such as $SiO_2$, $TiO_2$ or $ZrO_2$ by vapor deposition and an organic polymer thin film by coating, antistatic treatment and secondary treatment.

The following examples are provided for the purpose of further illustrating the present invention but are in no way to be taken as limiting.

EXAMPLES

Example 1

52.4 g (0.264 mol) of the following compound ($\alpha$):

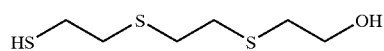

(α)

and 26.2 g (0.12 mol) of the following compound ($\beta$):

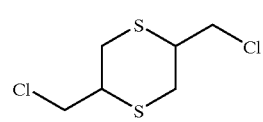

(β)

were heated and refluxed in 100 ml of methanol at 60° C. for 3 hours in the presence of 10.6 g (0.264 mol) of sodium hydroxide. After a reaction, the solvent was removed and 52 g (0.096 mol) of the following compound ($\gamma$) was obtained as a diol.

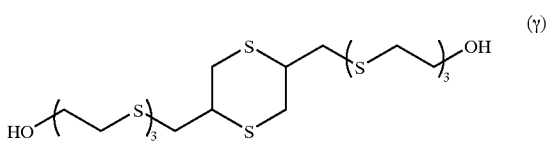

(γ)

It was confirmed that the above compound ($\gamma$) can be produced by the following process.

That is, 57.4 g (0.286 mol) of the following compound ($\delta$):

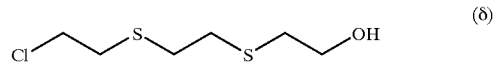

(δ)

and 27.6 g (0.13 mol) of the following compound ($\epsilon$):

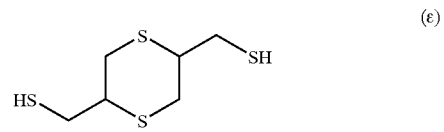

(ε)

were heated and refluxed in 100 ml of methanol at 60° C. for 1 hour in the presence of 11.4 g (0.286 mol) of sodium hydroxide, and then the solvent was removed to obtain 64 g (0.118 mol) of the compound ($\gamma$). Thereafter, 50 g (0.092 mol) of the above compound ($\gamma$), 0.5 g of cesium carbonate, 40 g (0.4 mol) of methyl methacrylate, 0.5 g of p-methoxyphenol and 15 ml of hexane were charged and reacted for 20 hours while methanol and hexane were co-boiled by heating at 90° C. to be removed. Subsequently, the removal of solid matter and the distillation off of the solvent were carried out and the reaction product was purified by chromatography on a silica gel to obtain 44 g (0.065 mol) of a white solid product ($\eta$). The yield was 54.2%. The yield as used herein is a value based on the compound ($\beta$) as a raw material.

According to the elemental analysis of this compound ($\eta$) the compound comprises 46.02%; of C, 6.64%; of H, 9.38%; of O, and 37.96%; of S, which well agree with 46.12%; of C, 6.55%; of H, 9.45%; of O, and 37.88%; of S, as calculation values for $C_{26}H_{44}O_4S_8$.

When the infrared absorption spectrum of the compound ($\eta$) was measured, as shown in FIG. 1, a strong peak derived from the carbonyl group of an ester bond was observed at around 1710 cm$^{-1}$ and a peak derived from a terminal unsaturated hydrocarbon group was observed at around 1635 cm$^{-1}$.

Figure 2:
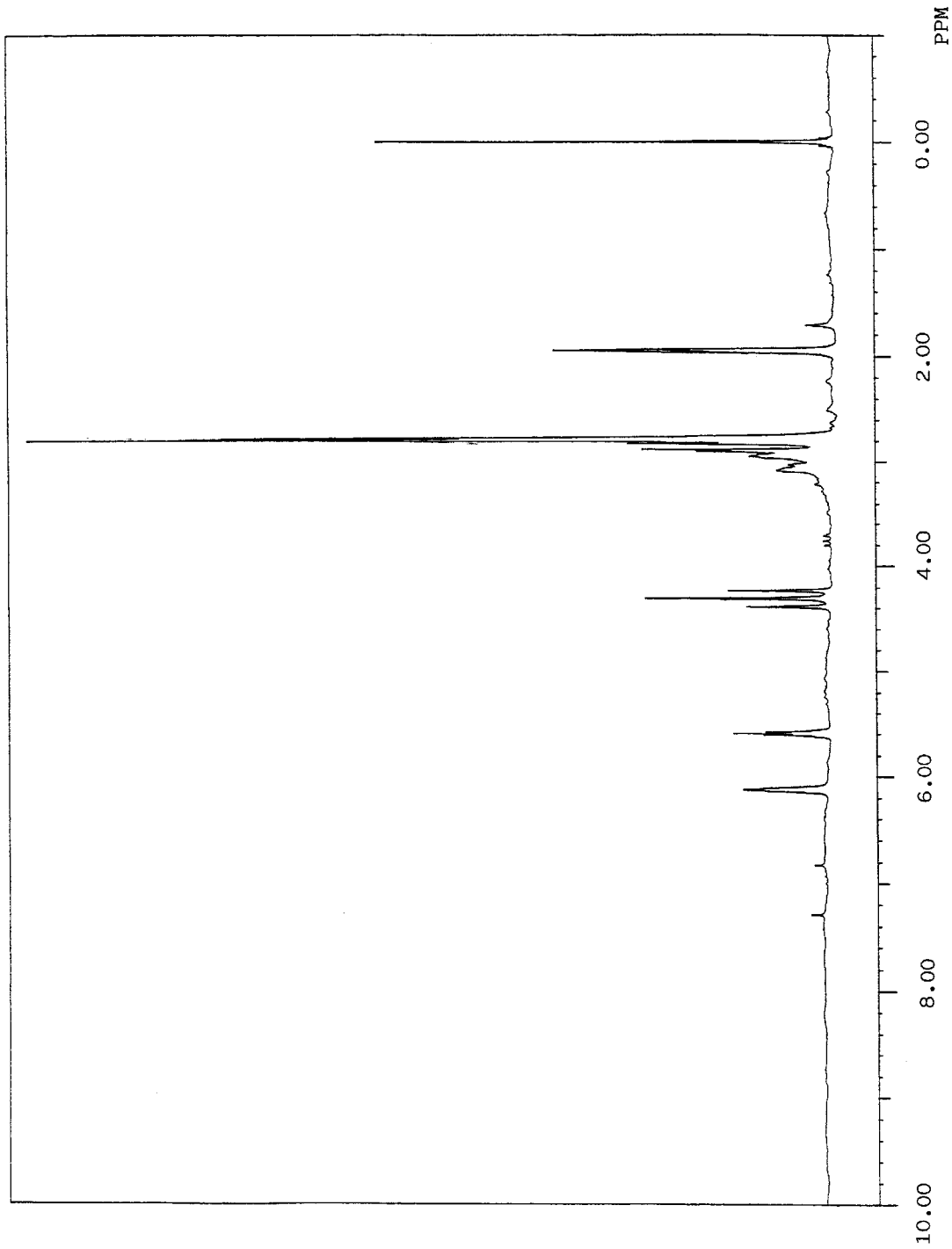
FIG. 2 shows the proton nuclear magnetic resonance spectrum of the compound (η) which is the product of Example 1.

Further, when the proton nuclear magnetic resonance spectrum of the compound was measured, as shown in FIG. 2, a 4H peak based on the proton of a terminal unsaturated hydrocarbon group was observed at around δ5.5 to 6.3 ppm, a 4H peak based on a proton bonded to the carbon of methylene adjacent to oxygen at around δ4.3 ppm, a 30H peak based on a proton bonded to the carbon of methylene adjacent to sulfur or the proton of a dithian ring at δ2.7 to 3.5 ppm, and a 6H peak based on the proton of a methyl group contained in a methacryl group at around δ2.0 ppm.

It was confirmed from the above results that the isolated product is a compound represented by the following structural formula ($\eta$).

(η)

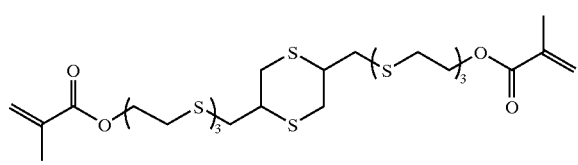

To check the storage stability of this product, it was kept in a constant temperature bath at 40° C. for 2 week to evaluate the gelation of the product after storage by the eye. As a result, the gelation was not observed at all.

Examples 2 to 19

Polymerizable sulfur-containing (meth)acrylates were synthesized by carrying the same reaction as in Example 1 except that compounds shown in Tables 1 to 6 were used as raw materials for the diol. When structural analysis was made on the obtained products using the same structural confirmation means as in Example 1, it was confirmed that they were compounds represented by structural formulas shown in Tables 1 to 6.

TABLE 1

| Example | raw material of diol | |
|---|---|---|
| 1 | *dithiane with two CH2Cl groups* | HS-(CH2CH2-S)2-CH2CH2-OH |
| 2 | *dithiane with CH2SH and HSCH2 groups* | Cl-(CH2CH2-S)5-CH2CH2-OH |
| 3 | *dithiane with CH2SH and HSCH2 groups* | Cl-CH2CH2-S-CH2CH2-OH |
| 4 | *dithiane with CH2SH and HSCH2 groups* | Cl-CH2CH2CH2-S-CH2CH2CH2-OH |
| 5 | *dithiane with CH2SH and HSCH2 groups* | Cl-CH2CH2-S-CH2CH2-OH ; Cl-(CH2CH2-S)2-CH2CH2-OH |

| Example | product | yield (%) |
|---|---|---|
| 1 | methacrylate-O-(CH2CH2-S)3-CH2-dithiane-CH2-(S-CH2CH2)3-O-methacrylate | 54.2 |
| 2 | methacrylate-O-(CH2CH2-S)6-CH2-dithiane-CH2-(S-CH2CH2)6-O-methacrylate | 46.3 |
| 3 | methacrylate-O-(CH2CH2-S)2-CH2-dithiane-CH2-(S-CH2CH2)2-O-methacrylate | 62.8 |

TABLE 1-continued
| | | |
|---|---|---|
| 4 | 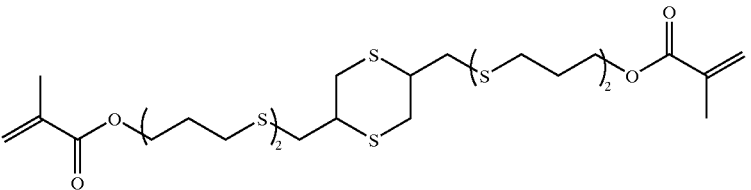 | 51.6 |
| 5 | 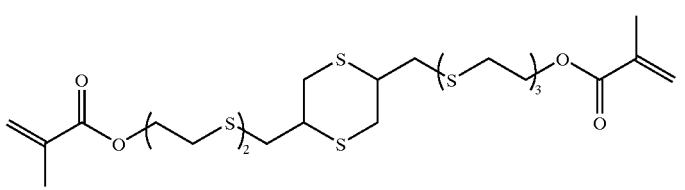 | 26.1 |
TABLE 2
| Example | raw material of diol | |
|---|---|---|
| 6 | 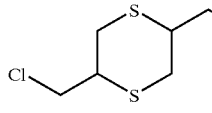 | 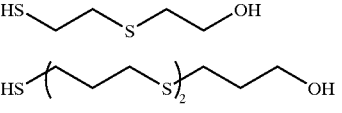 |
| 7 | 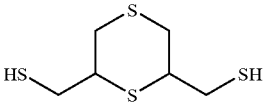 | 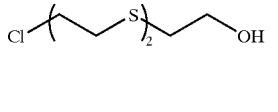 |
| 8 | 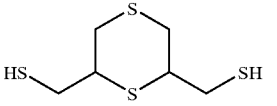 | 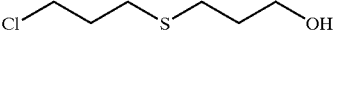 |
| 9 | 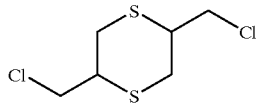 | 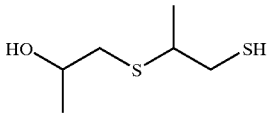 |
| Example | product | yield (%) |
|---|---|---|
| 6 | 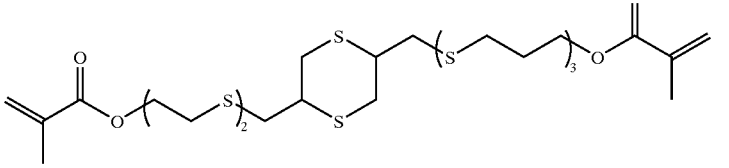 | 23.8 |
| 7 | 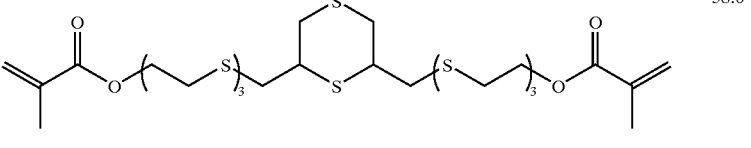 | 58.6 |
| 8 | 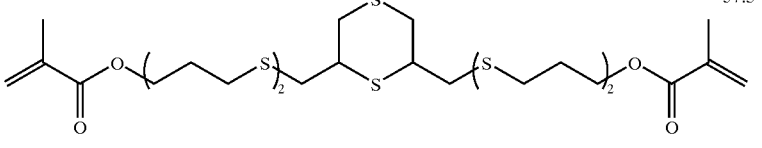 | 57.3 |

TABLE 2-continued
| | | yield (%) |
|---|---|---|
| 9 | 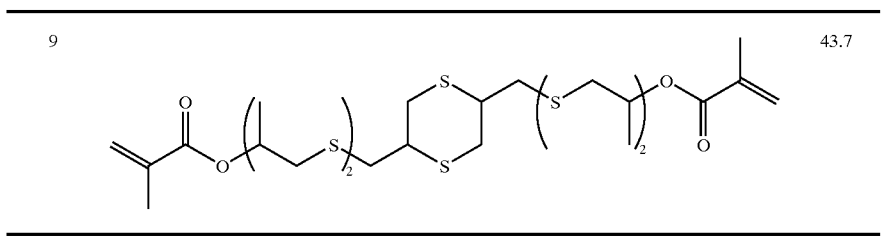 | 43.7 |
TABLE 3
| Example | raw material of diol | |
|---|---|---|
| 10 | (dithiane-dimethanethiol structure) | (HO-CH(Ph)-CH2-S-CH2-CH(Ph)-Cl) |
| 11 | (dithiane-dimethanethiol structure) | (HO-CH2-CH(SMe)-S-CH2-CH(SMe)-Cl) |
| Example | product | yield (%) |
|---|---|---|
| 10 | (dimethacrylate product with phenyl groups) | 50.6 |
| 11 | (dimethacrylate product with SMe groups) | 37.7 |

TABLE 4

| Example | raw material of diol | |
|---|---|---|
| 12 | [1,4-dithiane with CH₂Cl substituent, dimer structure] | HO-CH₂CH₂-SH |
| 13 | [1,4-dithiane with CH₂Cl substituent, dimer structure] | HO-CH₂CH₂-SH; HS-(CH₂CH₂-S)₂-CH₂CH₂-OH |

| Example | product | yield (%) |
|---|---|---|
| 12 | [dithiane-CH₂-S-CH₂CH₂-O-C(=O)-C(CH₃)=CH₂]₂ structure | 43.8 |
| 13 | CH₂=C(CH₃)-C(=O)-O-CH₂CH₂-(S-dithiane-CH₂)₂-S-CH₂CH₂-(S-CH₂CH₂)₂-O-C(=O)-C(CH₃)=CH₂ | 20.8 |

TABLE 5

| Example | raw material of diol | |
|---|---|---|
| 14 | HS-(dithiane-CH₂)-S-(CH₂-dithiane)-CH₂-SH structure | HO-CH₂CH₂-Cl |
| 15 | [S-CH₂CH₂-S-CH₂-dithiane-CH₂Cl]₂ structure | HO-CH₂CH₂-SH |
| 16 | (H₃C)₂-C-[C₆H₄-S-CH₂-dithiane-CH₂-SH]₂ structure | HO-CH₂CH₂-Cl |
| 17 | HS-CH₂-dithiane-CH₂-S-CH₂-dithiane-CH₂-SH structure | HO-CH(CH₃)-CH₂-Cl |

TABLE 5-continued
| Example | product | yield (%) |
|---|---|---|
| 14 | 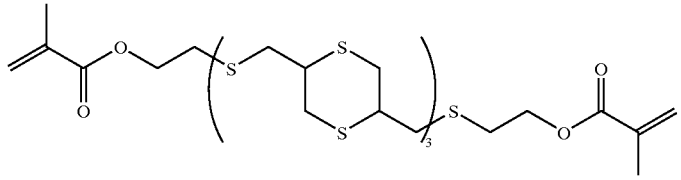 | 38.2 |
| 15 | 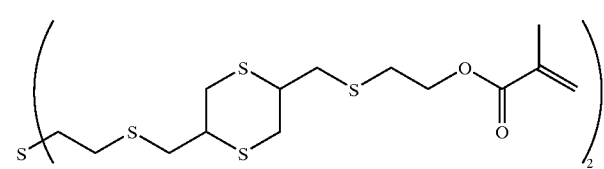 | 43.2 |
| 16 | 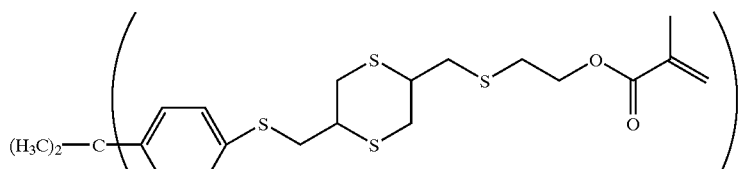 | 38.6 |
| 17 | 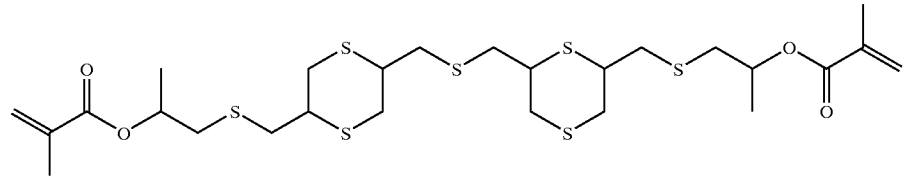 | 38.4 |
TABLE 6
| Example | raw material of diol |
|---|---|
| 18 | 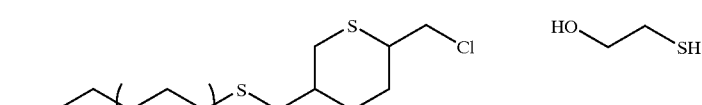 |
| 19 |  |

TABLE 6-continued

| Example | product | yield (%) |
|---|---|---|
| 18 | 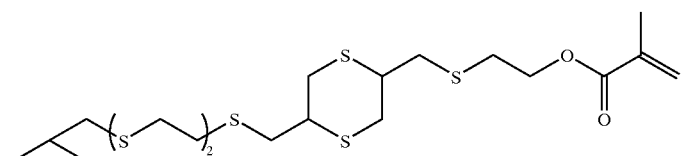 | 35.3 |
| 19 | 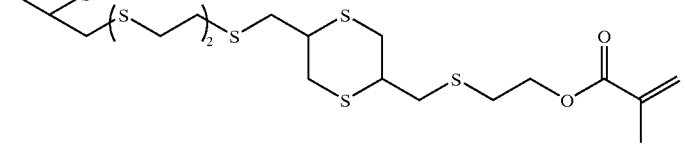 | 56.8 |

The elemental analytical values and characteristic peaks of the $^1$H-NMR spectrum and infrared absorption spectrum of these compounds are shown in Tables 7 to 9. Further, in order to confirm the storage stability of these compounds, they were kept in a constant temperature bath heated at 40° C. for 2 weeks to evaluate gelation after storage by the eye. The results of storage stability are shown in Tables 7 to 9. The evaluation criteria are as follows. (◯): gelation does not occur after 2 weeks of storage in constant temperature bath heated at 40° C. (×): gelation occurs after 2 weeks of storage in constant temperature bath heated at 40° C.

TABLE 7

| Example | elemental analysis | | | | | | | |
|---|---|---|---|---|---|---|---|---|
| | experimental value | | | | calculation value | | | |
| No. | C | H | O | S | C | H | O | S |
| 1 | 46.02 | 6.64 | 9.38 | 37.96 | 46.12 | 6.55 | 9.45 | 37.88 |
| 2 | 43.91 | 6.61 | 6.26 | 43.22 | 43.98 | 6.60 | 6.17 | 43.25 |
| 3 | 47.38 | 6.49 | 11.55 | 34.58 | 47.45 | 6.51 | 11.49 | 34.55 |
| 4 | 60.05 | 7.28 | 10.35 | 31.32 | 50.94 | 7.23 | 10.45 | 31.38 |
| 5 | 46.66 | 6.62 | 10.48 | 36.24 | 46.72 | 6.53 | 10.37 | 36.38 |
| 6 | 49.36 | 6.97 | 9.69 | 33.08 | 49.20 | 7.03 | 9.71 | 34.06 |
| 7 | 46.11 | 6.51 | 9.38 | 38.00 | 46.12 | 6.55 | 9.45 | 37.88 |
| 8 | 50.81 | 7.20 | 10.53 | 31.46 | 50.94 | 7.23 | 10.45 | 31.38 |

| Example No. | $^1$H-NMR(ppm) | IR(cm$^{-1}$) | storage stability |
|---|---|---|---|
| 1 | δ 1.0~3.5(36H) δ 4.0~4.6(4H) δ 5.0~7.0(4H) | around 1710 (carbonyl group) around 1635 (terminal unsaturated hydrocarbon group) | ◯ |
| 2 | δ 1.0~3.5(60H) δ 4.0~4.6(4H) δ 5.0~7.0(4H) | around 1710 (carbonyl group) around 1635 (terminal unsaturated hydrocarbon group) | ◯ |
| 3 | δ 1.0~3.5(28H) δ 4.0~4.6(4H) δ 5.0~7.0(4H) | around 1710 (carbonyl group) around 1635 (terminal unsaturated hydrocarbon group) | ◯ |
| 4 | δ 1.0~3.5(36H) δ 4.0~4.6(4H) δ 5.0~7.0(4H) | around 1710 (carbonyl group) around 1635 (terminal unsaturated hydrocarbon group) | ◯ |
| 5 | δ 1.0~3.5(32H) δ 4.0~4.6(4H) δ 5.0~7.0(4H) | around 1710 (carbonyl group) around 1635 (terminal unsaturated hydrocarbon group) | ◯ |
| 6 | δ 1.0~3.5(38H) δ 4.0~4.6(4H) δ 5.0~7.0(4H) | around 1710 (carbonyl group) around 1635 (terminal unsaturated hydrocarbon group) | ◯ |
| 7 | δ 1.0~3.5(36H) δ 4.0~4.6(4H) δ 5.0~7.0(4H) | around 1710 (carbonyl group) around 1635 (terminal unsaturated hydrocarbon group) | ◯ |
| 8 | δ 1.0~3.5(36H) δ 4.0~4.6(4H) δ 5.0~7.0(4H) | around 1710 (carbonyl group) around 1635 (terminal unsaturated hydrocarbon group) | ◯ |

TABLE 8

| Example | elemental analysis | | | | | | | |
|---|---|---|---|---|---|---|---|---|
| | experimental value | | | | calculation value | | | |
| No. | C | H | O | S | C | H | O | S |
| 9 | 50.99 | 7.35 | 10.33 | 31.33 | 50.94 | 7.23 | 10.45 | 31.38 |
| 10 | 64.07 | 6.15 | 7.52 | 22.26 | 64.15 | 6.09 | 7.43 | 22.33 |
| 11 | 42.05 | 6.06 | 8.62 | 43.27 | 42.13 | 5.98 | 8.63 | 43.26 |
| 12 | 46.84 | 6.18 | 10.38 | 36.60 | 46.87 | 6.22 | 10.41 | 36.50 |
| 13 | 45.81 | 6.29 | 8.73 | 39.17 | 45.74 | 6.31 | 8.70 | 39.25 |
| 14 | 45.33 | 6.08 | 8.11 | 40.48 | 45.42 | 6.10 | 8.07 | 40.41 |
| 15 | 45.66 | 6.23 | 8.85 | 39.26 | 45.74 | 6.31 | 8.70 | 39.25 |

| Example No. | $^1$H-NMR(ppm) | IR(cm$^{-1}$) | storage stability |
|---|---|---|---|
| 9 | δ 1.0~3.5(38H) δ 4.0~4.6(2H) δ 5.0~7.0(4H) | around 1710 (carbonyl group) around 1635 (terminal unsaturated hydrocarbon group) | ◯ |
| 10 | δ 1.0~3.5(24H) δ 4.0~4.6(4H) δ 5.0~7.0(4H) δ 7.0~9.0(20H) | around 1710 (carbonyl group) around 1635 (terminal unsaturated hydrocarbon group) 1650 to 1450 (aromatic cyclic) | ◯ |
| 11 | δ 1.0~3.5(36H) δ 4.0~4.6(4H) δ 5.0~7.0(4H) | around 1710 (carbonyl group) around 1635 (terminal unsaturated hydrocarbon group) | ◯ |

TABLE 8-continued

| | | | |
|---|---|---|---|
| 12 | δ 1.0~3.5(30H) | around 1710 (carbonyl group) | ○ |
| | δ 4.0~4.6(4H) | around 1635 (terminal unsaturated | |
| | δ 5.0~7.0(4H) | hydrocarbon group) | |
| 13 | δ 1.0~3.5(38H) | around 1710 (carbonyl group) | ○ |
| | δ 4.0~4.6(4H) | around 1635 (terminal unsaturated | |
| | δ 5.0~7.0(4H) | hydrocarbon group) | |
| 14 | δ 1.0~3.5(40H) | around 1710 (carbonyl group) | ○ |
| | δ 4.0~4.6(4H) | around 1635 (terminal unsaturated | |
| | δ 5.0~7.0(4H) | hydrocarbon group) | |
| 15 | δ 1.0~3.5(38H) | around 1710 (carbonyl group) | ○ |
| | δ 4.0~4.6(4H) | around 1635 (terminal unsaturated | |
| | δ 5.0~7.0(4H) | hydrocarbon group) | |

TABLE 9

| | elemental analysis | | | | | | | |
|---|---|---|---|---|---|---|---|---|
| Example | experimental value | | | | calculation value | | | |
| No. | C | H | O | S | C | H | O | S |
| 16 | 55.62 | 6.18 | 7.64 | 30.56 | 55.67 | 6.23 | 7.61 | 30.49 |
| 17 | 48.63 | 6.52 | 9.97 | 34.88 | 48.56 | 6.58 | 9.95 | 34.91 |
| 18 | 44.03 | 6.27 | 6.24 | 43.46 | 44.15 | 6.24 | 6.19 | 43.42 |
| 19 | 44.43 | 6.30 | 9.83 | 39.44 | 44.41 | 6.21 | 9.86 | 39.52 |

| Example No. | $^1$H-NMR(ppm) | IR(cm$^{-1}$) | storage stability |
|---|---|---|---|
| 16 | δ 1.0~3.5(36H) | around 1710 (carbonyl group) | ○ |
| | δ 4.0~4.6(4H) | around 1635 (terminal unsaturated | |
| | δ 5.0~7.0(4H) | hydrocarbon group) | |
| | δ 7.0~9.0(8H) | | |
| 17 | δ 1.0~3.5(36H) | around 1710 (carbonyl group) | ○ |
| | δ 4.0~4.6(2H) | around 1635 (terminal unsaturated | |
| | δ 5.0~7.0(4H) | hydrocarbon group) | |
| 18 | δ 1.0~3.5(56H) | around 1710 (carbonyl group) | ○ |
| | δ 4.0~4.6(4H) | around 1635 (terminal unsaturated | |
| | δ 5.0~7.0(4H) | hydrocarbon group) | |
| 19 | δ 1.0~3.5(32H) | around 1710 (carbonyl group) | ○ |
| | δ 4.0~4.6(4H) | around 1635 (terminal unsaturated | |
| | δ 5.0~7.0(4H) | hydrocarbon group) | |

Examples 20 to 45

The polymerizable sulfur-containing (meth)acrylates of the present invention obtained in Examples 1 to 19 were used and comonomers were added as components B and C as required to prepare curable compositions having monomer compositions shown in Tables 10 and 11, and the obtained curable compositions were polymerized and cured to obtain cured products.

Polymerization was carried out as follows. That is, 0.5 part by weight of t-butyl peroxyneodecanoate and 0.4 part by weight of 1,1,3,3-tetramethylbutyl peroxy-2-ethylhexanate were added as radical polymerization initiators to 100 parts by weight of each of the above curable compositions and mixed well. This mixture solution was injected into a mold composed of a gasket made from an ethylene-vinyl acetate copolymer and a glass plate and cast polymerized. An air oven was used for polymerization, and the inside temperature was gradually elevated from 33° C. to 90° C. over 17 hours and maintained at 90° C. for 5 hours. After the end of polymerization, the cast mold was taken out from the air oven and left in the air until it was cool enough and the cured product was taken out from the glass of the mold.

Abbreviations in Tables 10 and 11 stand for the following compounds.

Component A:
  polymerizable sulfur-containing (meth)acrylates in the present application produced in respective Examples Component B:
  GMA: glycidyl methacrylate
  3G: triethylene glycol dimethacrylate
  4G: tetraethylene glycol dimethacrylate Component C:
  BPEM: 2,2-bis(4-methacryloyloxy polyethoxyphenyl) propane(ethylene oxide chain average value of 2.6)
  BZMA: benzyl methacrylate
  St: styrene
  MS: α-methylstyrene

TABLE 10

| | monomer composition | | | physical properties of polymer | | | | |
|---|---|---|---|---|---|---|---|---|
| | (parts by weight) | | | refractive | Abbe's | light resistance | | |
| Ex. | A | B | C | index | number | (ΔYI) | odor | appearance |
| 20 | 1 (100) | — | — | 1.625 | 45 | 1.4 | ○ | achromatic and transparent |
| 21 | 1 (80) | — | BzMA (20) | 1.616 | 42 | 1.2 | ○ | achromatic and transparent |
| 22 | 2 (100) | — | — | 1.638 | 43 | 1.3 | Δ | achromatic and transparent |
| 23 | 3 (100) | — | — | 1.607 | 45 | 1.4 | ○ | achromatic and transparent |
| 24 | 4 (90) | GMA (10) | — | 1.598 | 46 | 1.3 | ○ | achromatic and transparent |
| 25 | 5 (90) | — | BPEM (10) | 1.616 | 42 | 1.2 | Δ | achromatic and transparent |
| 26 | 6 (95) | GMA (5) | — | 1.608 | 44 | 1.3 | Δ | achromatic and transparent |
| 27 | 7 (100) | — | — | 1.624 | 43 | 1.4 | ○ | achromatic and transparent |
| 28 | 7 (80) | — | BzMA (20) | 1.613 | 40 | 1.3 | ○ | achromatic and transparent |
| 30 | 8 (100) | — | — | 1.605 | 42 | 1.2 | Δ | achromatic and transparent |

TABLE 10-continued

| | monomer composition (parts by weight) | | | physical properties of polymer | | | | |
|---|---|---|---|---|---|---|---|---|
| Ex. | A | B | C | refractive index | Abbe's number | light resistance (ΔYI) | odor | appearance |
| 31 | 9 (100) | — | — | 1.603 | 43 | 1.3 | ○ | achromatic and transparent |
| 32 | 10 (100) | — | — | 1.655 | 38 | 1.3 | ○ | achromatic and transparent |
| 33 | 10 (80) | GMA (10) | BzMA (10) | 1.633 | 41 | 1.4 | ○ | achromatic and transparent |
| 34 | 11 (100) | — | — | 1.639 | 41 | 1.4 | Δ | achromatic and transparent |
| 35 | 12 (100) | — | — | 1.621 | 42 | 1.2 | ○ | achromatic and transparent |
| 36 | 12 (80) | — | BzMA (20) | 1.611 | 40 | 1.1 | ○ | achromatic and transparent |
| 37 | 13 (70) | — | MS (30) | 1.617 | 40 | 1.3 | Δ | achromatic and transparent |
| 38 | 14 (100) | — | — | 1.626 | 43 | 1.5 | ○ | achromatic and transparent |
| 39 | 15 (100) | — | — | 1.628 | 41 | 1.2 | ○ | achromatic and transparent |
| 40 | 15 (80) | — | BzMA (20) | 1.612 | 42 | 1.1 | ○ | achromatic and transparent |

Ex.: Example

TABLE 11

| | monomer composition (parts by weight) | | | physical properties of polymer | | | | |
|---|---|---|---|---|---|---|---|---|
| Ex. | A | B | C | refractive index | Abbe's number | light resistance (ΔYI) | odor | appearance |
| 41 | 16 (80) | 3G (20) | — | 1.607 | 42 | 1.5 | Δ | achromatic and transparent |
| 42 | 17 (80) | 4G (10) | St (10) | 1.604 | 39 | 1.3 | ○ | achromatic and transparent |
| 43 | 18 (100) | — | — | 1.640 | 41 | 1.2 | Δ | achromatic and transparent |
| 44 | 18 (80) | — | BzMA (20) | 1.623 | 40 | 1.4 | Δ | achromatic and transparent |
| 45 | 19 (100) | — | — | 1.629 | 40 | 1.3 | ○ | achromatic and transparent |
| C. Ex. 1 | compound (θ) (80) | — | BzMA (20) | 1.580 | 39 | 1.4 | ○ | achromatic and transparent |
| 2 | compound (κ) (100) | — | — | 1.66 | 31 | 4.1 | Δ | achromatic and transparent |
| 3 | compound (λ) (100) | — | — | 1.620 | 39 | 7.6 | × | achromatic and transparent |

Ex.: Example
C. Ex.: Comparative Example

The cured products obtained as described above were measured for their physical properties in accordance with the following test methods. The results are shown in Tables 10 and 11.

Refractive Index and Abbe's Number

The refractive index and Abbe's number at 20° C. are measured using the Abbe refractometer of Atago KK. Bromonaphthalene or methylene iodide is used as a contact solution. A higher refractive index and a larger Abbe's number are more preferred.

Light Resistance

A sample is set in the long-life xenon fade meter of Suga Shikenki Co., Ltd. and exposed to xenon light for 100 hours to measure YI of the sample with the color difference meter (SM-4) of Suga Shikenki KK. The light resistance is represented by an increase ΔYI from initial YI (YI: yellow index). It can be said that light resistance increases as ΔYI decreases.

Odor

An odor generated at the time of cutting with a diamond cutter or polishing with a edger is evaluated based on the following criteria.

(○): odorless
(Δ): smelling but not so bad.
(×): bad-smelling and making one sick Appearance judged visually.

Comparative Examples 1 to 3

Curable compositions having monomer compositions shown in Table 11 were prepared using the following compounds (θ), (κ) and (λ) as the component A:

(θ)

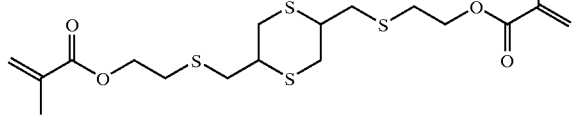

(κ)

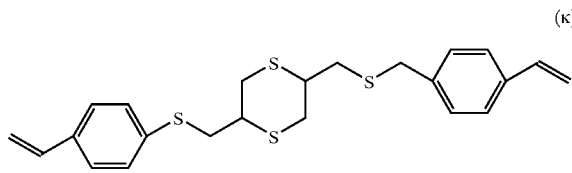

(λ)

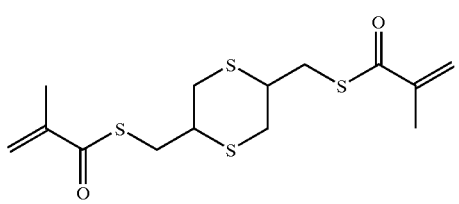

in place of the polymerizable sulfur-containing (meth) acrylates of the present invention to obtain cured products in the same manner as in Example 20. The obtained cured products were measured for their physical properties in the same manner as in Example 20. The results are shown in Table 11. The storage stabilities (measured in accordance with the method described in Example 1) of the compounds (θ) and (κ) were evaluated as ○ (gelation was not observed) and the storage stability of the compound (λ) was evaluated as × (gelation was observed).

When Examples 21, 28 and 36 which comprised 20 parts by weight of BZMA as a comonomer are compared with Comparative Example 1, it is understood that Examples have higher refractive indices and larger Abbe's numbers than Comparative Example. When Examples are compared with Comparative Example 2, it is understood that all the Examples are superior to Comparative Example 2 in balance between refractive index and Abbe's number. Further, when Examples are compared with Comparative Example 3, they do not differ from each other in refractive index and Abbe's number but Examples are superior to Comparative Example 3 in the storage stability of monomers and odor at the time of polishing cured products.

As described above, the polymerizable sulfur-containing (meth)acrylate of the present invention is useful as a monomer which gives a cured product having a high refractive index, a large Abbe's number and excellent light resistance. A cured product obtained from the polymerizable monomer rarely smells at the time of polishing. The monomer is hardly modified, that is, gelled after long-term storage.

Therefore, the cured product obtained by homopolymerizing the polymerizable sulfur-containing (meth)acrylate of the present invention or copolymerizing it with a comonomer is useful as an optical material, the best suitable for use as optical lenses such as spectacle lenses and lenses for optical instruments, and can be advantageously used in prisms, optical disk substrates, optical fibers and the like.

What is claimed is:

1. A polymerizable sulfur-containing (meth)acrylate represented by the following formula (1):

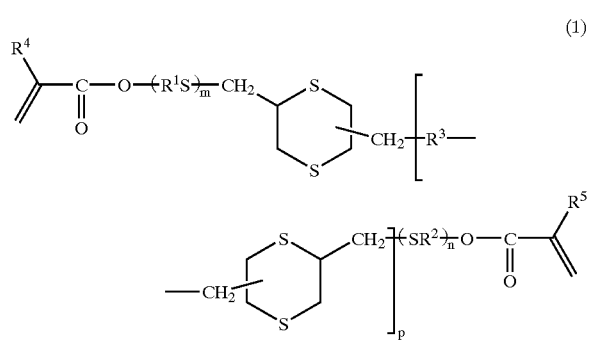

wherein $R^1$ and $R^2$ are each independently an alkylene group having 2 to 4 carbon atoms or arylene group having 6 to 12 carbon atoms, $R^3$ is a group represented by the following formula (a):

(wherein $R^6$ is an alkylene group having 2 to 4 carbon atoms, arylene group having 6 to 12 carbon atoms, aromatic heterocyclic group, or group represented by the following formula (b):

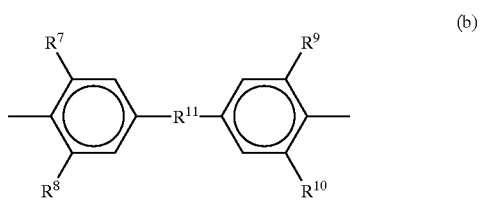

wherein $R^7$, $R^8$, $R^9$ and $R^{10}$ are each independently a halogen atom (excluding fluorine atom) or hydrogen atom, $R^{11}$ is an alkylene group having 1 to 3 carbon atoms or sulfur atom, and q is an integer of 0 to 4), $R^4$ and $R^5$ are each independently a hydrogen atom or methyl group, p is an integer of 0 to 6, and m and n are each independently an integer of 1 to 6, with the proviso that the above alkylene group, arylene group and aromatic heterocyclic group may be substituted with a substituent, and m and n are not "1" when p is "0".

2. The polymerizable sulfur-containing (meth)acrylate of claim 1 which is represented by the following formula (2):

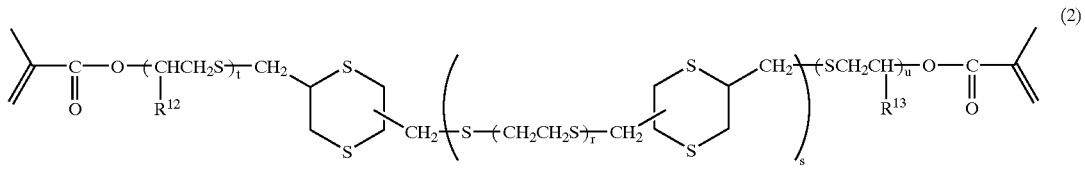

wherein $R^{12}$ and $R^{13}$ are each independently a hydrogen atom or methyl group, r is an integer of 0 to 2, s is an integer of 0 to 3, and t and u are each independently an integer of 1 to 4, with the proviso that t and u are not "1" when s is "0".

3. A polymerizable composition which comprises the polymerizable sulfur-containing (meth)acrylate represented by the above formula (1) of claim 1, in an amount of 10 to 98 wt % and other polymerizable monomer copolymerizable with the above (meth)acrylate in an amount of 90 to 2 wt % based on the total of the (meth)acrylate and the monomer.

4. The polymerizable composition of claim 2, which comprises the polymerizable sulfur-containing containing (meth)acrylate represented by the above formula (2) in an amount of 10 to 98 wt % and other polymerizable monomer copolymerizable with the above (meth)acrylate in an amount of 90 to 2 wt % based on the total of the (meth)acrylate and the monomer.

5. The polymerizable composition of claim 3, wherein the other polymerizable monomer is at least one compound selected from the group consisting of (meth)acrylic esters, thio(meth)acrylic esters, allyl compounds, aromatic vinyl compounds, urethane (meth)acrylates having at least two (meth)acrylate groups in the molecule, and epoxy (meth)acrylates having at least two (meth)acrylate groups in the molecule.

6. A cured material for use as an optical material which comprises the cured product of the polymerizable composition of claim 3.

7. A cured material for use as an optical material which comprises the cured product of the polymerizable composition of claim 4.

8. A cured material for use as an optical material which comprises the cured product of the polymerizable composition of claim 5.

9. An optical lens which comprises the cured material for use as an optical material of claim 6.

10. An optical lens which comprises the cured material of claim 7.

11. An optical lens which comprises the cured material of claim 8.

* * * * *